US 6,697,675 B1

(12) United States Patent
Safarevich et al.

(10) Patent No.: US 6,697,675 B1
(45) Date of Patent: Feb. 24, 2004

(54) LASER WELDED JOINT FOR IMPLANTABLE LEAD

(75) Inventors: Sergey Safarevich, Valencia, CA (US); Benedict L. Gomperz, North Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 252 days.

(21) Appl. No.: 09/881,179

(22) Filed: Jun. 14, 2001

(51) Int. Cl.[7] ................................................. A61N 1/08
(52) U.S. Cl. ...................................................... 607/116
(58) Field of Search ........................... 439/874; 607/37, 607/116, 119, 122, 126, 127, 131

(56) References Cited

U.S. PATENT DOCUMENTS

| | | |
|---|---|---|
| 1,390,596 A | 9/1921 | Thornton, Jr. |
| 1,745,180 A | 1/1930 | Mischler .................... 439/874 |
| 1,908,859 A | 5/1933 | O'Neill ...................... 439/874 |
| 1,977,846 A | 10/1934 | Febrey .......................... 29/148 |
| 2,878,461 A | 3/1959 | Friedmann et al. ......... 339/275 |
| 3,656,092 A | 4/1972 | Swengel, Sr. et al. ... 339/213 T |
| 3,676,575 A | 7/1972 | Weaver et al. |
| 4,034,152 A * | 7/1977 | Warner ..................... 174/94 R |
| 4,161,952 A | 7/1979 | Kinney et al. .............. 128/786 |
| 4,352,714 A | 10/1982 | Patterson et al. .......... 156/626 |
| 4,360,031 A | 11/1982 | White ......................... 128/786 |
| 4,784,161 A | 11/1988 | Skalsky et al. ............. 128/785 |
| 4,844,099 A | 7/1989 | Skalsky et al. ............. 128/785 |
| 4,917,106 A | 4/1990 | Olivier ....................... 128/785 |
| 4,966,565 A | 10/1990 | Dohi .......................... 439/874 |
| 5,115,818 A | 5/1992 | Holleman et al. .......... 128/784 |
| 5,251,643 A * | 10/1993 | Osypka ...................... 607/122 |
| 5,259,395 A | 11/1993 | Li ............................... 607/131 |
| 5,385,578 A * | 1/1995 | Bush et al. ................. 607/122 |
| 5,489,294 A | 2/1996 | McVenes et al. ........... 607/120 |
| 5,522,872 A | 6/1996 | Hoff ........................... 607/119 |
| 5,522,874 A | 6/1996 | Gates ......................... 607/127 |
| 5,522,875 A | 6/1996 | Gates et al. ................ 607/127 |
| 5,569,883 A * | 10/1996 | Walter et al. ............. 174/84 R |
| 5,571,146 A | 11/1996 | Jones et al. .................. 607/37 |
| 5,676,694 A * | 10/1997 | Boser et al. ................ 607/122 |
| 5,716,390 A | 2/1998 | Li ............................... 607/127 |
| 5,728,149 A * | 3/1998 | Laske et al. ................ 607/122 |
| 5,746,616 A | 5/1998 | Mar ............................ 439/245 |
| 5,877,472 A * | 3/1999 | Campbell et al. ...... 219/121.64 |
| 6,456,888 B1 * | 9/2002 | Skinner et al. ............. 607/116 |

* cited by examiner

*Primary Examiner*—George R. Evanisko
*Assistant Examiner*—Frances P. Oropeza (57) ABSTRACT

A method of joining a wound element, or coiled wire strand, and a mating component, or integral ledge member, of a body implantable lead assembly wherein the former has a interior passage and an end portion adapted to be received by the latter. In one embodiment, the integral ledge member is formed with an integral collar spaced from a terminal end thereof. The wound element is placed about the receiving portion and over the terminal end of the mating component and against the collar. The components are then joined by thermally fusing them together, preferably by means of a laser. If the collar and the wound element are fabricated of the same alloy, the thickness of the collar and the diameter of the coiled wire strand are designed to be substantially equal. If the components are fabricated of dissimilar alloys, then the thickness of the collar is relatively dimensioned with respect to the diameter of the strand in proportion to the relative thermal diffusivity of the alloy of the collar and of the alloy of the coiled wire strand. In another embodiment, a ring member is placed about, and in engagement with, the receiving portion of the mating component. Then the components are joined, by thermally fusing them together, preferably by targeting a laser beam directly on the ring member, without regard to whether the components are fabricated of the same alloy or of different alloys.

10 Claims, 6 Drawing Sheets

LASER WELDED JOINT FOR IMPLANTABLE LEAD

FIELD OF THE INVENTION

The present invention relates generally to lead assemblies for connecting implantable medical devices with selected body tissue to be stimulated by such devices, and more particularly to techniques for providing a secure electrical and mechanical connection between wound elements, such as coil conductors, and mating parts such as electrodes, sensors and the like, employed within such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled or wound conductor surrounded by an insulating tube or sheath couples the connector pin at the proximal end with the electrode at the distal end.

When terminating a wound conductor to an associated electrical element such as a proximal end connector pin, a heart tissue stimulating electrode at the distal end of the lead, a blood oxygen sensor, or other such elements within the lead assembly, there is often no way to statistically ascertain the structural integrity of the termination. These joints must have a high degree of reliability for the implantable product to be acceptable for long term implants such as endocardial type pacing leads. In the past, the only way to verify the joint was to immobilize the mating part and pull on the wound conductor and this technique has been used as the chief test method. The major problem with this approach is that as the winding is pulled unequal tension is applied to the individual strains of the wound conductor. As increased tension is applied to the coil, often one strain breaks sooner than the others yielding erratic test results. The present invention provides an approach that overcomes this test method problem while at the same time providing a very reliable and secure connection between a wound element and a mating component.

Perhaps the primary concern with the laser welding of windings and their electrical connectors is that there must exist a balance between the energy delivered to the respective metal masses. In many known constructions, the laser must simultaneously heat the relatively large mass of the connector and the relatively small mass of the wire ends of the wound conductor.

Another problem associated with connections between wound elements and mating components in present day lead assemblies arises from the use of different alloys for the wound elements and mating components. Since dissimilar alloys have different melt temperatures and other thermal properties, such connections are difficult to weld. Moreover, as lead sizes decrease, problems of manufacturability arise. This is particularly true where crimping is employed to secure the wound component to a mating element. See, for example, U.S. Pat. No. 4,953,564 which discloses a cardiac pacing lead having an extendible fixation helix electrode that is mechanically and electrically connected to a rotatable conductor coil by squeezing the helix and coil together between a crimping sleeve and a crimping core. As the sizes of body implantable leads and their constituent parts become smaller, crimping becomes more difficult because the crimping tools cannot be made sufficiently small. Moreover, the same number of lead windings are not always subjected to the crimping action so that failure stress differs from lead to lead.

Some selective examples of the patented prior art will now be mentioned briefly. U.S. Pat. No. 5,569,883 to Walter et al. discloses laser welding a wire coil to an intermediate ring or the like. U.S. Pat. No. 5,571,146 to Jones et al. discloses laser welding dissimilar materials by means of an aperture within a lead. U.S. Pat. No. 5,385,578 to Bush et al. discloses laser welding a wire coil to a sleeve.

It was with knowledge of the foregoing state of the technology that the present invention has been conceived and is now reduced to practice.

SUMMARY OF THE INVENTION

The present invention relates to a method of joining a longitudinally extending wound element, or coiled wire strand having a wire end portion, and a mating component of a body implantable lead assembly. In one instance, the mating component may include an integral outwardly projecting ledge member with an aperture for receiving the wire end portion; in another instance, an elongated ribbon member has an aperture for receiving the wire end portion of the wound element; in yet another instance, an elongated ribbon member is turned back onto itself at an end to form parallel spaced apart courses defining a slot therebetween for receiving the wire end portion; in still another instance, a tubular member has a continuous sidewall, an aperture through the sidewall, and a window in the sidewall adversely positioned with respect to the aperture, the wire end portion projecting from the exterior of the tubular member through the aperture and into the interior of the tubular member; and in yet another instance, a tubular member has a continuous sidewall, a first aperture through the sidewall for freely receiving therethrough the wire end portion of the wound element, and a second aperture through the sidewall adversely positioned with respect to the first aperture, also for freely receiving therethrough the wire end portion of the wound element. In each instance, the wire end portion and the mating component are then thermally fused together, preferably by means of a laser.

As already noted, a primary purpose of the invention is to improve a laser weld between a winding and a connector and to achieve this result, the laser beam energy should be distributed equally between the wire and the connector. Formerly, the common weld joint typically comprised a winding screwed onto a cylindrical connector. The very last wind (that is, the wire ends) sets against a shoulder. The shoulder and the last wind (the wire ends) are then welded together in an appropriate manner.

The problem which the present invention solves stems from the fact that the connector requires more laser energy to melt than does the wire. During welding, the laser beam heats both welded components, the connector and the wire (winding) simultaneously. The wire melts and the connector melts, but the wire has a smaller metal mass than the connector. As such, the wire accumulates heat very quickly and the wire can melt easily. The connector has much more metal mass by reason of which heat is drawn out of the weld region. This makes it difficult to melt the metal and to create a weld joint. Therefore, the connector requires more laser energy to melt than does the wire. To have a reliable weld, the beam energy must be specifically balanced between the connector and the wire. Proper beam targeting requires placement of the laser beam not equally on the joint such that more energy is focused on the shoulder side than on the wire. However, it is most difficult for a production line operator to properly target the laser beam on the joint and such failure to properly target the laser beam causes rejects resulting from wire melt down, component overheating, lack of weld, and so forth.

Then, too, a difference in material thermal properties multiplies the energy balance problem. For example, platinum requires much more energy to melt than the commonly used alloy MP35N. Proper beam targeting on dissimilar materials becomes even more critical and difficult to achieve a solid weld than when targeting on similar materials.

Also, this kind of weld configuration has one more problem: wires neck down. When wire ends melt, the melted metal spreads over the connector surface and lack of melting metal occurs. After weld solidification the wire ends attached to the weld have necks down. The neck down makes the weld weaker.

The invention related to the laser weld joint (lead winding to connector) of dissimilar or similar materials.

The connector has a slot and the wire ends go through this slot. The connector/winding joint is designed to with ability to target the laser beam towards to the wire ends coming out of the slot. The wire ends are exposed over the connector to equalize the mass of welded materials of wire and connector. The beam should be directed towards to the wire ends to melt wires ends first to create an extra melted material to protect the wire from neck down and the connector from possible burn through.

The laser beam energy applied to the weld joint melts the wire ends very fast. The melted metal slips down creating a puddle over the surface of the connector. The weld puddle protects the wire in the slot from direct impact of laser beam. The laser beam heats the connector and the puddle fusing components together. The melted metal fills the gaps between wires in the slot and creates some positive weld reinforcement. The wire ends are protected from neck down making the weld stronger.

Figure 4:
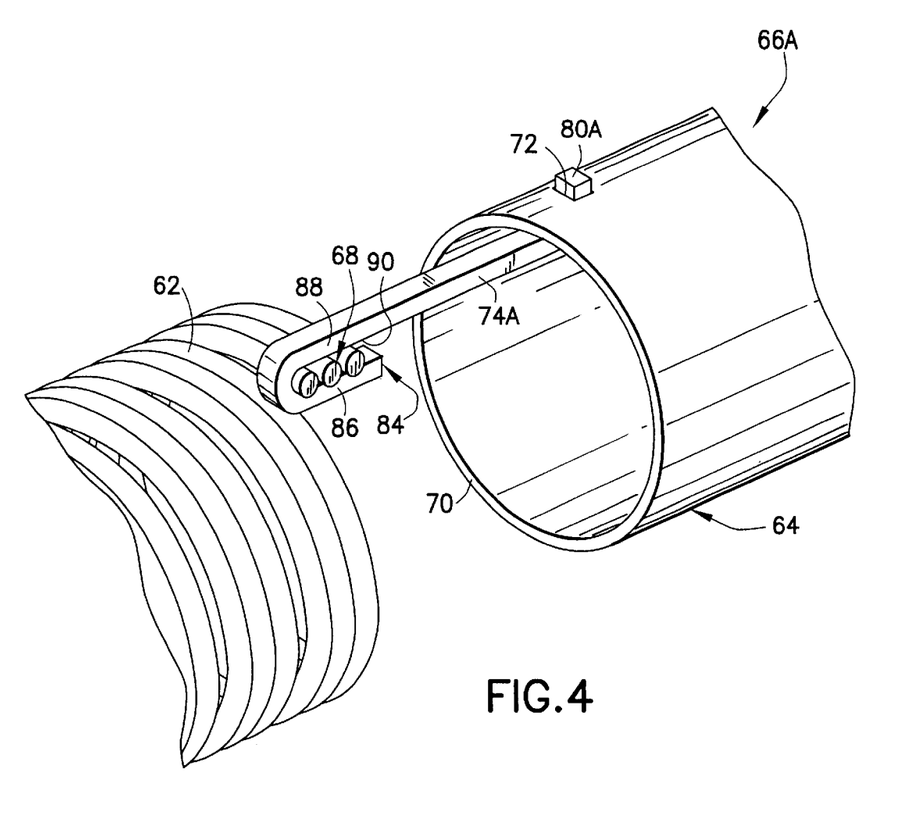
FIG. 4 is a perspective view of still another embodiment of a lead assembly of the present invention awaiting the application of a laser beam for performing the fusing operation.

On FIG. 4 the winding is welded to the transition element, which could be welded to any kind of, connectors rings or other implantable lead component.

All shown weld joints can be welded with equal energy distribution between the wires and connector (or transition element) because the joints with exposed wire ends creates correct heat flow balance between the wires and connector. The length of the exposed wire ends can regulate the heat flow balance. Even if the components are made from different materials with different thermal properties the heat flow can be balanced.

Higher thermal properties of material require less mass of material involved in the welding process. For example, if the connector made from Platinum (high thermal properties) and the winding from MP35N (low thermal properties) to compensate for heat flow misbalance (Platinum requires more energy), the exposed wire ends should be longer than in case when the components made from the same material.

Lower thermal properties of material require more mass of material involved in the welding process. If the connector made from MP35N (low thermal properties) and the winding from Platinum (high thermal properties) to compensate for heat flow misbalance (Platinum requires more energy), the exposed wire ends should be shorter than in case when the components made from the same material.

A primary feature, then, of the present invention is the provision of a significantly improved technique for providing a secure electrical and mechanical connection between wound elements, such as coil conductors, and mating parts such as electrodes, sensors and the like, employed within such lead assemblies.

Another feature of the present invention is the provision of such a technique employing a laser.

Still another feature of the present invention is the provision of such a technique which can achieve a satisfactory connection whether or not the alloys of which the components are fabricated are the same or dissimilar.

Yet another feature of the present invention is the provision of a technique of joining a wound element and a mating component of a body implantable lead assembly, where, in one instance, the mating component includes an integral outwardly projecting ledge member with an aperture for receiving the wire end portion.

Still a further feature of the present invention is the provision of a technique of joining a wound element and a mating component of a body implantable lead assembly, where, in another instance, the mating component includes an elongated ribbon member with an aperture for receiving the wire end portion of the wound element.

Still another feature of the present invention is the provision of such a technique of joining a wound element and a mating component of a body implantable lead assembly, where, in yet another instance, an elongated ribbon member is turned back onto itself at an end to form parallel spaced apart courses defining a slot therebetween for receiving the wire end portion.

Yet a further feature of the present invention is the provision of such a technique of joining a wound element and a mating component of a body implantable lead assembly, where, in still another instance, a tubular member has a continuous sidewall, an aperture through the sidewall, and a window in the sidewall adversely positioned with respect to the aperture, the wire end portion projecting from the exterior of the tubular member through the aperture and into the interior of the tubular member.

Still another feature of the present invention is the provision of such a technique of joining a wound element and a mating component of a body implantable lead assembly, where, in yet another instance, a tubular member has a continuous sidewall, a first aperture through the sidewall for freely receiving therethrough the wire end portion of the wound element, and a second aperture through the sidewall adversely positioned with respect to the first aperture, also for freely receiving therethrough the wire end portion of the wound element.

Still another feature of the present invention is the provision of such a technique of joining a wound element and a mating component of a body implantable lead assembly, where, in each instance, the wire end portion and the mating component are then thermally fused together, preferably by means of a laser.

Yet another of the present invention is the provision of such a technique wherein the resulting connection has an improved weld quality over known techniques, exhibits increased strength, guards against component overheating, and results in an improved appearance.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

As noted above, of primary concern with laser welding of two metals is that there must exist a balance between energy to be delivered to the metal masses. Known connections between lead wire ends (usually a multifilar winding) to the shoulder of an electrode mount or connector is a circumferential weld. The problem with this type of weld is that the laser beam must heat a large mass of connector in order to obtain a satisfactory melt to heat and cause fixation of the wire ends. This technique is time consuming, has a tendency of overheating of the components being joined, particularly the wire winding, and has inconsistent results (i.e., reliability defects).

Alternately, spot welding has the advantages of less concern for overheating. However, current techniques of spot welding (for example, a weld on each wire end) have had inconsistent results. Filars do not always line up appropriately and/or don't get welded consistently. Disadvantages of this technique include misbalancing of energy; also, it is time consuming to target the energy beam at the exact locations needed.

Each of these techniques has been implemented with such inconsistent results, that throughput in production varies greatly. What is needed is a high reliability weld connection with increased manufacturability, that is, repeatability and reduced assembly time. These benefits are provided by the present invention.

Figure 1:
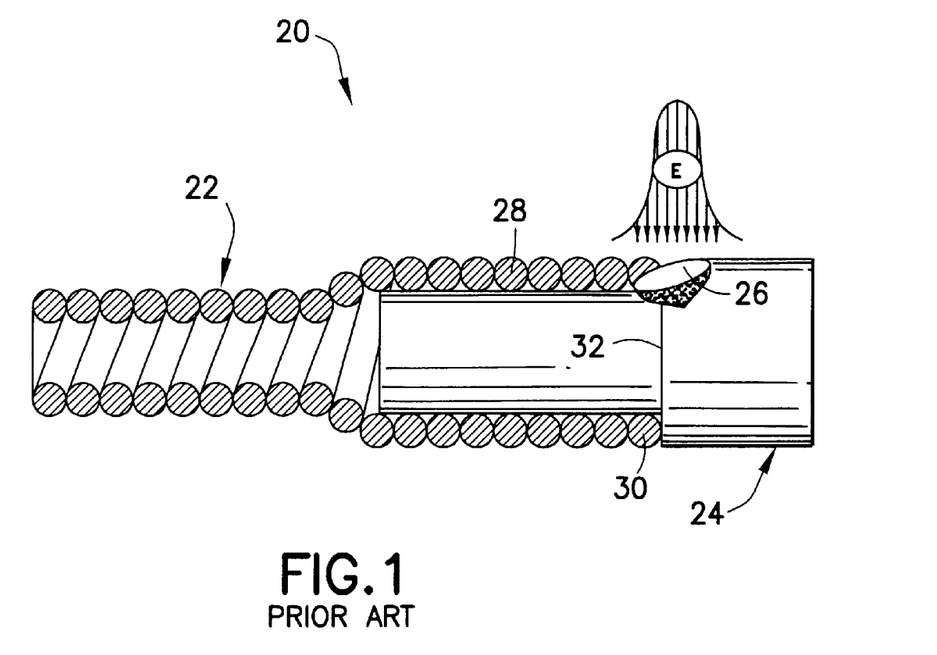
FIG. 1 is a diagrammatic side elevation view of a known laser weld assembly between a multi wire winding and a connector.

Turn now to the drawings and, initially, to FIG. 1 which generally illustrates a conventional circumferential laser weld assembly 20 between a multi wire winding 22 and a connector 24. To achieve this weld assembly 20, weld spots 26 obtained by use of a laser represented by a beam E, should be distributed around the periphery of the connector to melt together each wire strand 28 and the connector 24 itself. The common weld assembly comprises the winding 22 screwed or otherwise applied onto the cylindrical connector 24. The very last wind (wire ends 30) butts up against a shoulder 32 of the connector. The shoulder 32 and the last wind (wire ends 30) are thereby welded together.

As earlier explained, the connector 24 requires more laser energy to melt than does the wire strand 28 and the weld region needs more melted metal to increase strength of the weld assembly. During welding, the laser beam E melts both the connector 24 and the winding 22. The wire possesses less metal mass than does the connector. As such, the winding accumulates heat very quickly and the wire strands 28 can melt easily. The melted metal from the winding spreads over the connector forming the weld spot 26. A lack of melted metal creates wire "neck down" and negative weld reinforcement, which reduces the strength of weld joint. The connector has much more metal mass, which means it draws the heat out of the weld area. Unfortunately, this condition makes it difficult to melt the metal to fuse the components together. Therefore, the connector requires more energy from the laser beam E to melt than does the winding. To achieve a reliable weld, the beam energy must be specifically balanced between the connector and the winding. The proper beam targeting requires placement of the laser beam unequally on the joint such that more energy is on the shoulder side than on the wire. However, it is difficult for the assembly line operator to properly target the laser beam on the joint. A difference in material thermal properties further magnifies the energy balance problem. For example, platinum requires much more energy to melt than does MP35N, a high corrosion resistant stainless steel used for implantable devices including leads. If a joint comprises MP35N wire and a platinum connector it will need a greater misbalance of energy to melt the components equally. Proper beam targeting required to achieve a solid weld becomes more critical with dissimilar materials than with similar materials.

Figures 2A, 2B:
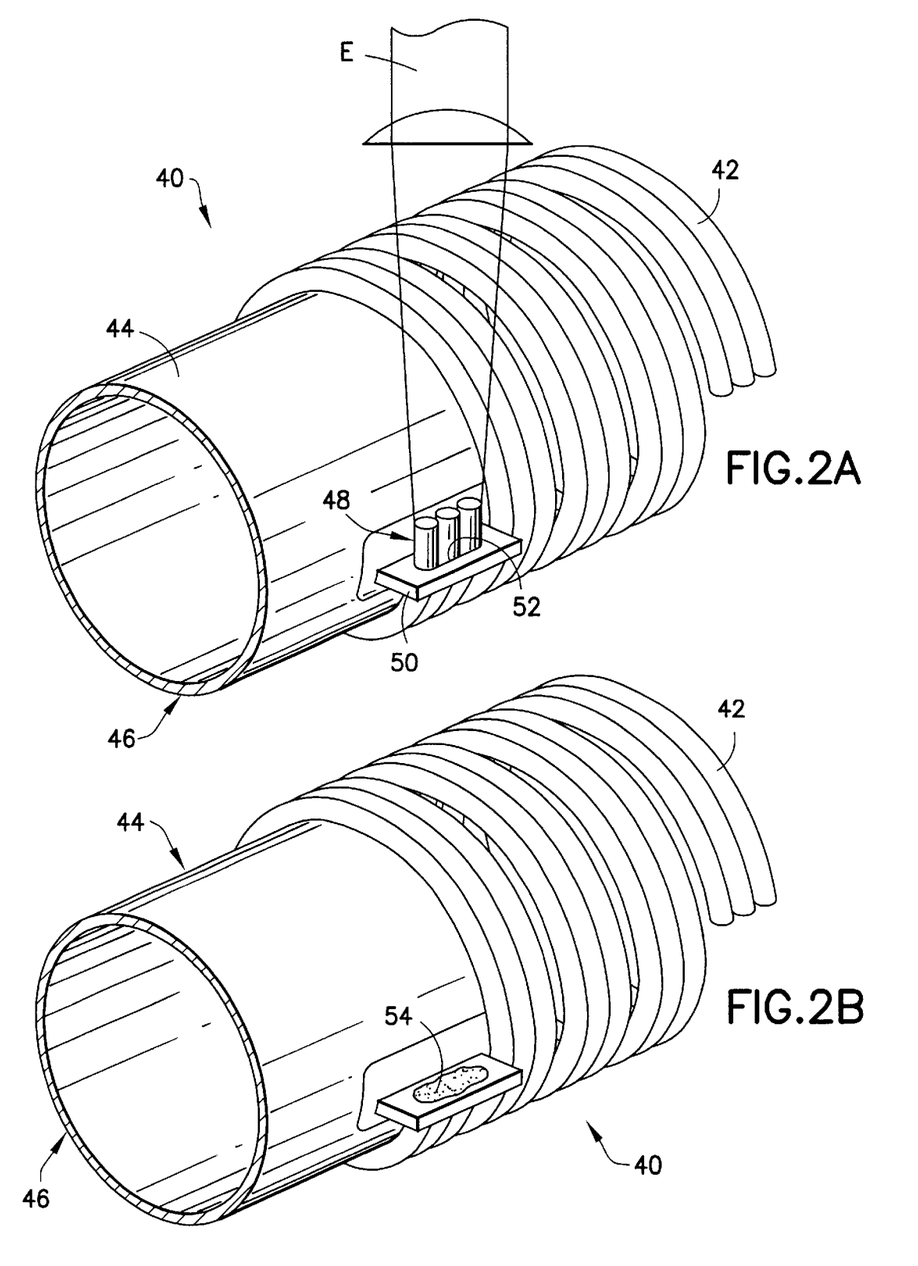
FIG. 2A is a perspective view of one embodiment of a lead assembly of the present invention depicting the application of a laser beam for performing the fusing operation.
FIG. 2B is a perspective view, similar to FIG. 2A, depicting the resulting joint.

Turn now to FIGS. 2A and 2B which illustrate a joint 40 connecting a wound element 42 and a mating component 44 of a body implantable lead assembly 46. The wound element 42 extends to a wire end portion 48. The mating component 44, which is illustrated as tubular, includes an integral outwardly projecting ledge member 50 with a through aperture 52 for receiving the wire end portion 48 of the wound element 42. When the mating component 44 and the wound element 42 are so positioned, a laser beam E is focused onto the wire end portion 48, thereby melting the wire end portion and forming a puddle 54 on the ledge member 50. Subsequently, the puddle 54 thermally fuses resulting in a solid connection between the wound element 42 and the mating component 44.

Figure 3:
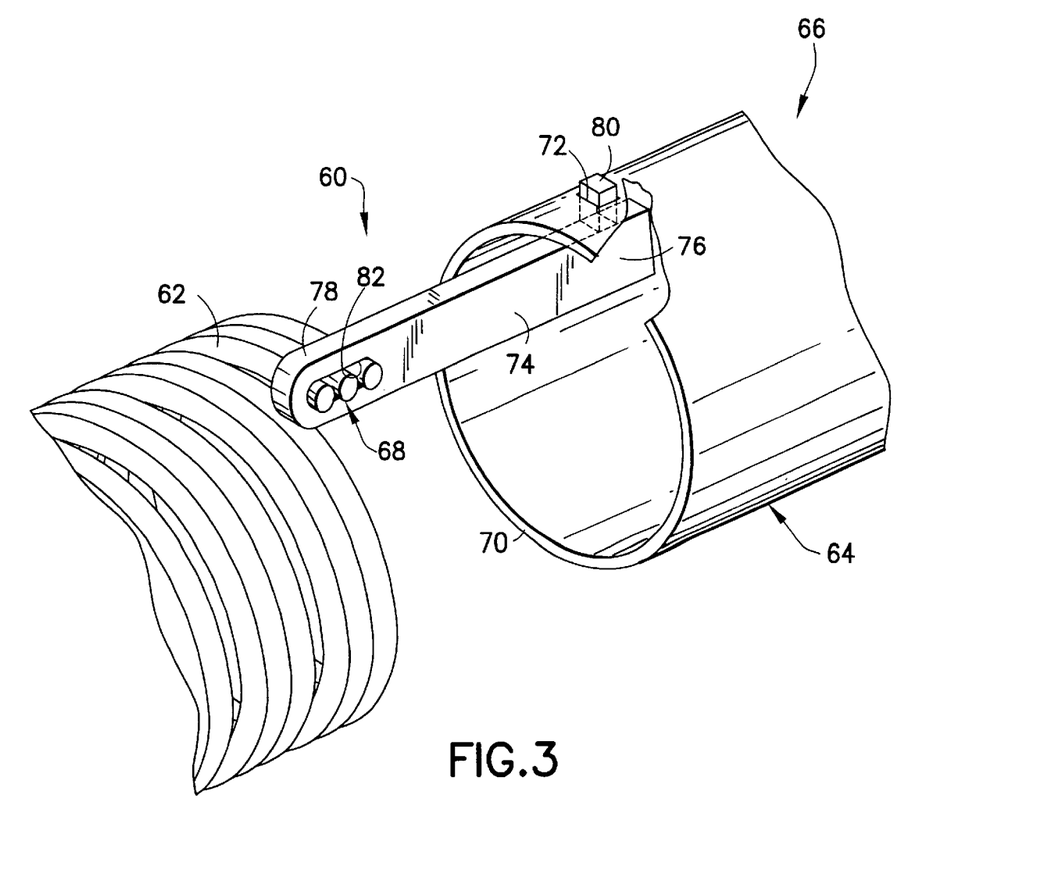
FIG. 3 is a perspective view of another embodiment of a lead assembly of the present invention awaiting the application of a laser beam for performing the fusing operation.

In FIG. 3, a joint 60 is illustrated connecting a wound element 62 and a mating component 64 of a body implantable lead assembly 66. The wound element 62 extends to a wire end portion 68. The mating component 64, which is illustrated as tubular, extends to a terminal end 70 and has an orifice 72 spaced from the terminal end. An elongated ribbon member 74 extends between first and second ends 76, 78, respectively, and has an outwardly projecting post 80 at the first end received in the orifice 72 and suitably fused to the tubular member or mating component 64. The elongated ribbon member 74 has an aperture 82 through the second end 78 for receiving the wire end portion 68 of the wound element 62.

As with the embodiment of FIGS. 2A and 2B, when the wire end portion 68 and the ribbon member 74 and mating component 64 are positioned as illustrated in FIG. 3, a laser beam is focused onto the wire end portion 68, thereby melting the wire end portion and forming a puddle (not shown in this instance). Subsequently, the puddle thermally fuses resulting in a solid connection between the wound element 62 and the ribbon member 74 and the mating component 64.

In FIG. 4, an assembly generally similar to that illustrated in FIG. 3 is presented. In this instance, however, a modified ribbon member 74A is used which is of slimmer construction than the ribbon member 74. In this instance, an end 84 of the ribbon member 74A is turned back onto itself at an end spaced from the terminal end 70 of the mating component 64 to form a pair of parallel spaced apart courses 86, 88 defining a slot 90 therebetween for receiving the wire end portion 68 of the wound element 62. As with the embodiment of FIG. 3, when the wire end portion 68 and the ribbon member 74A and mating component 64 are positioned as illustrated in FIG. 4, a laser beam is focused onto the wire end portion 68, thereby melting the wire end portion and forming a puddle (again not shown in this instance). Subsequently, the puddle thermally fuses resulting in a solid connection between the wound element 62 and the ribbon member 74A and the mating component 64.

Figure 5A:
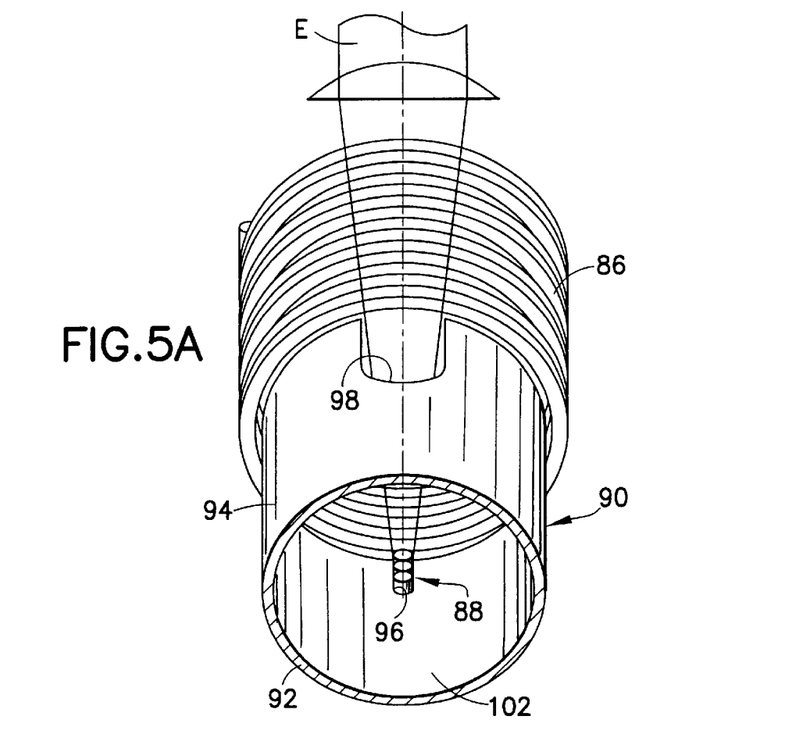
FIG. 5A is a perspective view of yet another embodiment of a lead assembly of the present invention depicting the application of a laser beam for performing the fusing operation.
Figure 5B:
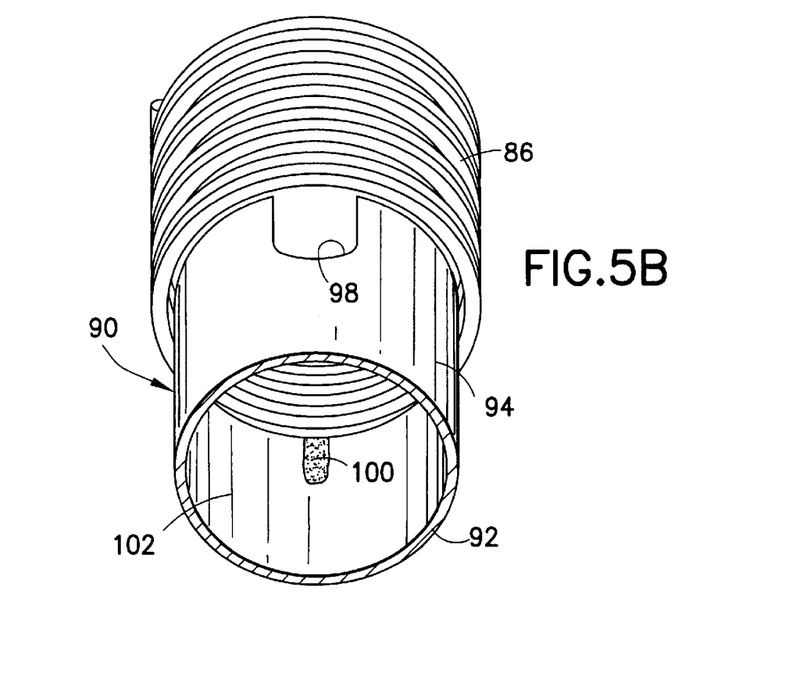
FIG. 5B is a perspective view, similar to FIG. 5A, depicting the resulting joint.

In FIGS. 5A and 5B, as in the preceding embodiments, a wound element 86 extends to a wire end portion 88. In this instance, a mating component 90 includes a tubular member 92 having a continuous sidewall 94. An aperture 96 extends through the sidewall 94 for freely receiving therethrough the wire end portion 88 of the wound element 86 (FIG. 5A). A window 98 extends through the sidewall 94 and is adversely positioned, that is, oppositely or diametrically positioned in the event the tubular member 92 is a cylinder, with respect to the aperture 96. With this construction, a laser beam E is targeted through the window 98 onto the wire end portion 88 projected through the aperture 96, the wire end portion 88 projecting inwardly from a location outside of the tubular member 92. As in the previously described embodiments, the laser beam E is focused onto the wire end portion 88 thereby melting the wire end portion and forming a puddle 100 on an interior surface 102 of the tubular member 92. Subsequently, the puddle 100 thermally fuses resulting in a solid connection between the wound element 86 and the mating component 90.

Figure 6A:
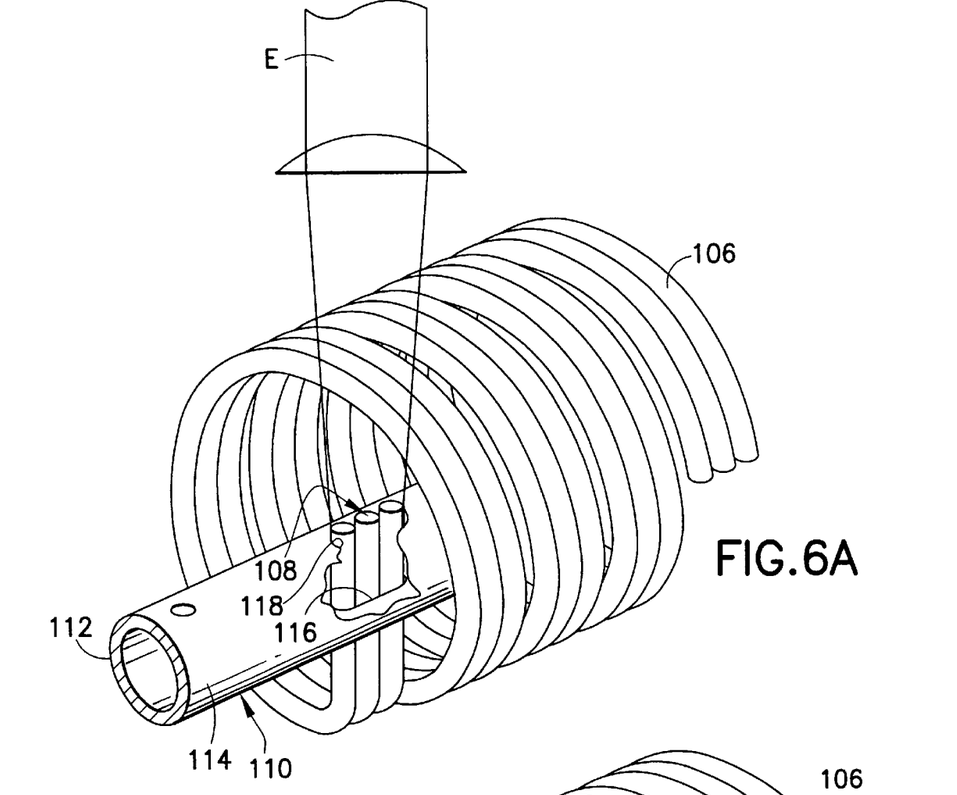
FIG. 6A is a perspective view of a further embodiment of a lead assembly of the present invention depicting the application of a laser beam for performing the fusing operation.
Figure 6B:
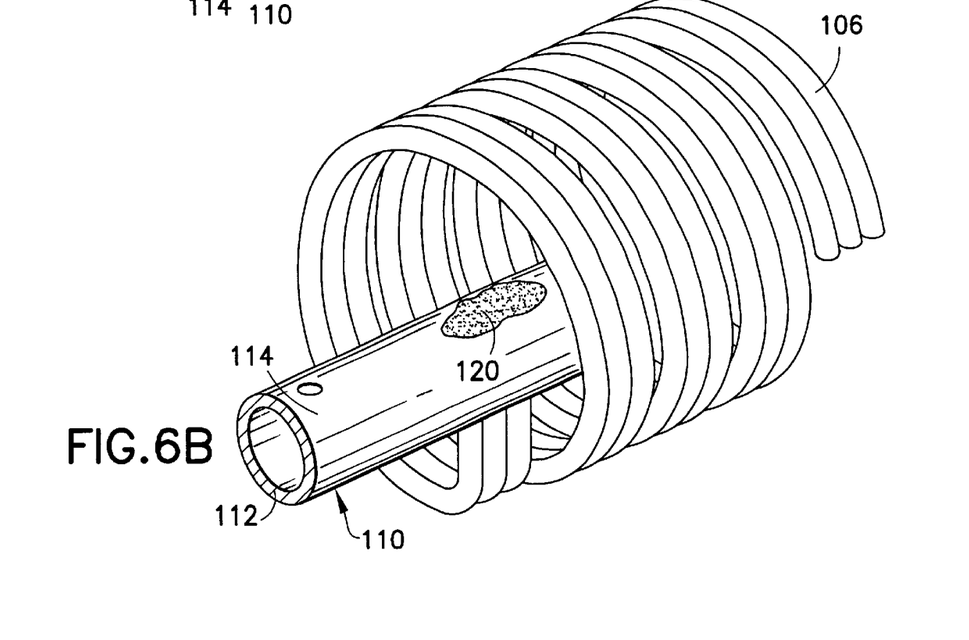
FIG. 6B is a perspective view, similar to FIG. 6A, depicting the resulting joint.

Once again, In FIGS. 6A and 6B, as in the preceding embodiments, a wound element 106 extends to a wire end portion 108. In this instance, a mating component 110 includes a tubular member 112 which has a continuous sidewall 114 and a first aperture 116 through the sidewall for freely receiving therethrough the wire end portion 108 of the wound element 106. The tubular member 112 has a second aperture 118 through the sidewall 114 adversely positioned with respect to the first aperture 116, also for freely receiving therethrough the wire end portion 108 of the wound element 106. As in the previously described embodiments, the laser beam E is focused onto the wire end portion 108 thereby melting the wire end portion and forming a puddle 120 on the surface of the sidewall 114 of the tubular member 112. Subsequently, the puddle 120 thermally fuses resulting in a solid connection between the wound element 106 and the mating component 110.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A joint comprising:
   a wound element extending to a wire end portion; and
   a mating component of a body implantable lead system, the mating component having an aperture to receive the end portion of the wound element, the mating component and the wire end portion of the wound element being integrally joined together by directing a laser beam substantially parallel to a longitudinal axis of the wire end portion to melt the wire end portion of the wound element and the mating component and the subsequent thermal fusion thereof;
   wherein the mating component includes a radially outwardly projecting ledge member with the aperture therethrough for receiving the wire end portion of the wound element; and
   wherein the mass of the radially outwardly projecting ledge member is substantially the same as the mass of the wire end portion to be melted such that thermal fusion requires equal energy distribution between the radially outwardly projecting ledge member and the wire end portion to be melted.

2. A joint as set forth in claim 1, wherein the wound element and the mating component are made, selectively, of the same metallic alloy.

3. A joint as set forth in claim 1 wherein the radially outwardly projecting ledge member is rectangularly shaped.

4. A joint as set forth in claim 1 wherein the mating component is a tubular body.

5. A joint as set forth in claim 4 wherein the radially outwardly projecting ledge member extends perpendicularly to an outer surface of the tubular body.

6. A joint comprising:
   a wound element extending to a wire end portion; and
   a mating component of a body implantable lead system having an aperture to receive the wire end portion of the would element, the mating component and the wire end portion of the wound element being integrally joined together by directing a laser beam substantially parallel to a longitudinal axis of the wire end portion to melt the wire end portion of the wound element and the mating component and the subsequent thermal fusion thereof;
   wherein the mating component includes a tubular member having a continuous sidewall, the aperture through the sidewall, and a window in the sidewall adversely positioned with respect to the aperture;

wherein the wire end portion of the wound element projects from the exterior of the tubular member through the aperture and into the interior of the tubular member; and wherein a laser beam is targeted through the window and onto the wire end portion projected through the aperture from a location outside of the tubular member.

7. A joint as set forth in claim 6 wherein the window is larger than the aperture.

8. A joint comprising:

a wound element extending to a wire end portion; and a mating component of a body implantable lead system thermally fused with the wound element, the mating component comprising:

a radially outwardly projecting ledge member;

an aperture through the radially outwardly projecting ledge member, the aperture to receive the wire end portion, the radially outwardly projecting ledge member and the wire end portion being integrally joined together by directing a laser beam substantially parallel to a longitudinal axis of the wire end portion to melt the wire end portion and the radially outwardly projecting ledge member;

wherein the wire end portion is relatively dimensioned with respect to the radially outwardly projecting ledge member in proportion to relative thermal properties of the wire end portion and the outwardly projecting ledge member to balance heat flow.

9. A joint as set forth in claim 8 wherein the wire end portion and the radially outwardly projecting ledge member comprise a same metallic alloy and wherein a mass of the wire end portion is substantially the same as a mass of the radially outwardly projecting ledge member to balance the heat flow.

10. A joint as set forth in claim 8 wherein the thermal properties of the wire end portion is greater than the thermal properties of the radially outwardly projecting ledge member and wherein the mass of the wire end portion is less than the mass of the radially outwardly projecting ledge member to balance the heat flow.

* * * * *